United States Patent [19]

De Lacharriere et al.

[11] Patent Number: 5,866,168

[45] Date of Patent: *Feb. 2, 1999

[54] DERMATOLOGICAL/PHARMACEUTICAL COMPOSITIONS COMPRISING LANTHANIDE, MANGANESE, TIN, ZINC, YTTRIUM, COBALT, BARIUM AND/OR STRONTIUM SALTS AS SUBSTANCE P ANTAGONISTS

[75] Inventors: Olivier De Lacharriere, Paris; Lionel Breton, Versailles, both of France

[73] Assignee: Société L'Oréal S.A., Paris, France

[ * ] Notice: The term of this patent shall not extend beyond the expiration date of Pat. No. 5,851,556.

[21] Appl. No.: 740,311

[22] Filed: Oct. 28, 1996

[30] Foreign Application Priority Data

Oct. 26, 1995 [FR] France ................................. 95 12656

[51] Int. Cl.⁶ .................................................. A61K 33/32
[52] U.S. Cl. ......................... 424/639; 424/600; 424/617; 424/646; 424/650; 424/677; 424/715; 424/718; 424/722
[58] Field of Search .................................. 424/722, 715, 424/709, 677, 663, 600, 617, 639, 650, 646, 718

[56] References Cited

U.S. PATENT DOCUMENTS

| | | | |
|---|---|---|---|
| 3,519,711 | 7/1970 | Svigals | 424/659 |
| 3,772,431 | 11/1973 | Mlkvy et al. | 424/44 |
| 3,888,976 | 6/1975 | Mlkvy et al. | 424/44 |
| 4,477,439 | 10/1984 | D'Alelio | 424/604 |
| 4,711,780 | 12/1987 | Fahim | 424/145 |
| 4,735,802 | 4/1988 | Le | 424/682 |
| 4,943,432 | 7/1990 | Biener | 424/647 |
| 4,980,184 | 12/1990 | Gordon | 426/335 |
| 4,986,981 | 1/1991 | Glace et al. | 424/50 |
| 5,047,409 | 9/1991 | Di Schiena et al. | 514/275 |
| 5,079,010 | 1/1992 | Natterer | 424/617 |
| 5,091,171 | 2/1992 | Yu et al. | 424/642 |
| 5,132,119 | 7/1992 | Lee | 424/646 |
| 5,202,130 | 4/1993 | Grant et al. | 424/617 |
| 5,296,476 | 3/1994 | Henderson | 514/574 |
| 5,593,992 | 1/1997 | Adams et al. | 514/235.8 |
| 5,716,625 | 2/1998 | Hahn et al. | 424/401 |

FOREIGN PATENT DOCUMENTS

| | | |
|---|---|---|
| 0085579 | 8/1983 | European Pat. Off. . |
| 0135312 | 3/1985 | European Pat. Off. . |
| 0217975 | 4/1987 | European Pat. Off. . |
| 0 401 503 | 4/1990 | European Pat. Off. . |
| 0439640 | 8/1991 | European Pat. Off. . |
| 0451300 | 10/1991 | European Pat. Off. . |
| 0459890 | 12/1991 | European Pat. Off. . |
| 0 522 808 | 7/1992 | European Pat. Off. . |
| 0586929 | 3/1994 | European Pat. Off. . |
| 5394 | 10/1967 | France . |
| 2122613 | 9/1972 | France . |
| 2184890 | 6/1978 | France . |
| 3338957 | 5/1985 | Germany . |
| 0280692 | 7/1990 | Germany . |
| 0297062 | 1/1992 | Germany . |
| 4315866 | 5/1994 | Germany . |
| 1072355 | 6/1964 | United Kingdom . |
| 2271774 | 4/1994 | United Kingdom . |
| WO 83/01252 | 4/1983 | WIPO . |
| WO87/01935 | 10/1986 | WIPO . |
| 91/01624 | 2/1991 | WIPO . |
| 91/02538 | 3/1991 | WIPO . |
| WO93/01165 | 7/1992 | WIPO . |
| WO 93/14084 | 7/1993 | WIPO . |
| 94/09798 | 5/1994 | WIPO . |
| WO 96/19183 | 6/1996 | WIPO . |
| WO 96/19184 | 6/1996 | WIPO . |
| WO 96/19928 | 6/1996 | WIPO . |

OTHER PUBLICATIONS

Maison G. deNavarre, *The Chemistry and Manufacture of Cosmetics,* 2nd Ed. vol. IV, p. 1261 (1975).

Alexander A. Fisher, "Irritant Reactions from Topical Urea Preparations Used for Dry Skin Advantages of a Urea–Free 'Dead Sea Salt' Cream", *Current Contact News,* vol. 18, pp.761–772 (1976).

*The United States Pharmacopeia,* "Alumina/Drug Substances and Dosage Form", pp. 20 and 22 (1975).

*Nordia Briefs,* "A Salt–Containing Cream for Dry Skin", No. 484, Jan. 1978.

*Cosmetic Counter,* vol. 109, Oct. 1994.

Jancso–Gabor, "Action of rare earth metal complexes on neurogenic as well as on bradykinin–induced inflammation", *J. Pharm. Pharmac.,* 22:366–371 (1970).

"La peau sensible, un authentique syndrome clinique", *Le Quotidien du Medecin,* No. 5747, Dec. 6, 1995; Cosmetologie, *Therapeutique,* No. 1511, Dec. 17, 1995.

Uy Dong Sohn et al, "Agonist–Independent, Muscle–Type–Specific Signal Transduction Pathways in Cat Esophageal and Lower Esophageal Sphincter Circular Smooth Muscle", *J. of Pharmacology & Experimental Therapeutics,* 273:481–491 (1995).

Mitsuo Ishizawa, "Contractile Responses of Longitudinal Muscle Strip to 5–HT and Influences of Divalent Cations in the Guinea–Pig Isolated Colon", *J. Smooth Muscle Res.,* 30:65–72 (1994).

(List continued on next page.)

*Primary Examiner*—Shelley A. Dodson
*Assistant Examiner*—Michael A. Williamson
*Attorney, Agent, or Firm*—Burns, Doane, Swecker & Mathis, L.L.P.

[57] ABSTRACT

Dermatological/pharmaceutical compositions, well suited for the therapeutic treatment of and/or alleviation of pain associated with at least one of the skin disorders, zona, poszoster, scald or burns, demodicidosis, skin ulcer, fibrosis, hypertrophic cicatrization and/or acne rosacea, comprise an effective substance P antagonist amount of at least one salt of yttrium, lanthanum, cerium, praseodymium, neodymium, promethium, samarium, europium, gadolinium, terbium, dysprosium, holmium, erbium, thulium, ytterbium, lutetium, tin, zinc, manganese, cobalt, barium, strontium, or mixture thereof, in a dermatologically/pharmaceutically acceptable medium therefor.

19 Claims, No Drawings

OTHER PUBLICATIONS

H. Goodman, *Cosmetic Dermatology,* First Edition, Fourth Impression, p. 181 (1936).

*Martindale,* The Extra Pharmacopoeia, Twenty–seventh Edition, The Pharmaceutical Press, London, pp. 219, 1775 and 1814 (1977).

*McGraw–Hill Dictionary of Scientific and Technical Terms,* Fifth Edition, pp. 109 and 332.

Sohn et al, Different Receptors Activate a Different Single G–Protein in Esophageal. (Gis) and in LES (Gq) Circular Smooth Muscle, *Gastroenterology,* vol. 104 (1993).

S.M. Moussaoui et al, *Br. J. Pharmacol.,* "A non–peptide $NK_1$–receptor antagonist, RP 67580, inhibits neurogenic inflammation postsynaptically", vol. 109, No.1, 1993, pp. 259–265.

J. Wallengren, *Br. J. Dermatol.,* "Substance P antagonist inhibits immediate and delayed type cutaneous hypersensitivity reactions", vol. 124, No. 4, 1991, pp. 324–328.

J. Wallengren et al, *Contact Dermatitis,* "Some neuropeptides as modulators of experimental contact allergy", vol. 19, No. 5, 1988, pp. 351–354.

T. Lotti et al, *J. Am. Acad. Dermatol.,* "Treatment of aquagenic pruritus with topical capsaicin cream", vol. 30, No. 2PT1, Feb. 1994, pp. 232–235.

T. Sakurada et al, *Brain Res.,* "A selective and extremely potent antagonist of the neurokinin–1 receptor", vol. 593, No. 2, 1992, pp. 319–322.

K. Folkers et al, *Proc. Natl. Acad. Sci. USA,* "Spantide II, an effective tachykinin antagonist having high potency", vol. 87, No. 12, 1990, pp. 4833–4855.

Rajadhyaksha, *Chemical Abstracts,* vol. 107, #223281 (1987).

DiSchiena, *Chemical Abstracts,* vol. 106, #107768 (1987).

Smith et al, *Chemical Abstract,* vol. 114, #206554 (1991).

Dufetal et al, *Chemical Abstracts,* vol. 116, #135998 (1992).

British Medical Journal (England), vol. 4, Nov. 1975, p. 264.

Chemical Abstracts, vol. 122, No. 16, Apr. 1995, Columbus, Ohio, abstract No. 196540.

Chemical Abstracts, vol. 95, No. 22, Nov. 1981, Columbus, Ohio, abstract No. 192217.

Chemical Abstracts, vol. 120, No. 17, Apr. 1994, Columbus, Ohio, abstract No. 210122.

DERMATOLOGICAL/PHARMACEUTICAL COMPOSITIONS COMPRISING LANTHANIDE, MANGANESE, TIN, ZINC, YTTRIUM, COBALT, BARIUM AND/OR STRONTIUM SALTS AS SUBSTANCE P ANTAGONISTS

BACKGROUND OF THE INVENTION

1. Technical Field of the Invention

The present invention relates to novel dermatological/pharmaceutical compositions comprising at least one lanthanide, manganese, tin, zinc, yttrium, cobalt, barium or strontium salt as a substance P antagonist, for the treatment of and/or alleviation of pain associated with at least one of the following skin disorders, including those of the scalp and mucous membranes: zona, poszoster, scald or burns, demodicidosis, skin ulcer, fibrosis and/or controlling hypertrophic cicatrization and/or treating acne rosacea.

2. Description of the Prior Art

Polypeptides belonging to the tachykinin family exist in mammals which induce rapid contractions of the smooth muscle fibers. Exemplary compounds of this family include β-neurokinin, α-neurokinin and substance P.

Substance P is a polypeptide chemical species (undecapeptide), produced and released by a nerve ending. The location of substance P is specific to the neurons, both in the central nervous system and in the organs at the periphery. Thus, very many organs or tissues receive afferences of substance P neurons; these are especially the salivary glands, stomach, pancreas, intestine (in the latter, the distribution of substance B is superposed on the intrinsic Meissner and Auerbach nervous plexus), cardiovascular system, thyroid gland, skin, iris and ciliary bodies, bladder and, obviously, the central and peripheral nervous systems.

By virtue of the ubiquitous distribution of substance P, very many disorders are associated with an excessive synthesis and/or release of substance P.

Substance P is involved, in particular, in the transmission of pain (dental, cutaneous, tympanic) and in diseases of the central nervous system (for example anxiety, psychoses, neuropathies, neurodegenerative disorders of the Alzheimer senile dementia type, dementia in Aids patients, Parkinson's disease, Down's syndrome, Korsakoff's syndrome, multiple scleroses, schizophrenia, psychotic diseases), in respiratory diseases (such as, for example, bronchial pneumonia, cough, emphysema, bronchiolitis) and inflammatory diseases (such as, for example, rheumatoid arthritis), in allergic syndromes (for example asthma, allergic rhinitis, allergic pharyngitis, urticaria, eczematous dermatitis), in gastrointestinal diseases (such as, for example, ulcers, colitis, Crohn's disease, gastritis, gastroenteritis, intestinal spasticities), in skin disorders (such as, for example, psoriasis, prurigenous diseases, herpes, photodermatosis, atopic dermatitis, contact dermatitis, lichens, prurigos, pruritus, rosacea, ulcers, zona, demodicidoses, acne rosacea, sensitive skins, dartres, solar and emotional erythemas, insect burns), in fibroses and other collagen maturation disorders (such as, for example, scleroderma), in cardiovascular diseases, vasospastic disorders (such as, for example, migraine, Raynaud's disease), in immunological disorders, in disorders of the urinary or genital tract (such as, for example, incontinence, cystitis), in rheumatic diseases, in certain dermatological diseases (such as eczema) and in ophthalmological conditions (such as, for example, conjunctivitis, uveitis, ocular pruritus, blepharitis, irritations and ocular pain).

The administration of a substance P antagonist is one of the therapeutic alternatives which are effective in all of the conditions and afflictions indicated above.

By "substance P antagonist" is intended any compound or species capable of partially, or even completely inhibiting the biological effect of substance P. In particular, for a substance to be recognized as a substance P antagonist, it must induce a coherent pharmacological response (including or otherwise its binding to the substance P receptor), in particular in one of the following tests:

(a) the antagonist substance must reduce the extravasation of the plasma across the vascular wall induced by capsaicin or by an antidromic nerve stimulation, or, alternatively;

(b) the antagonist substance must cause inhibition of the contraction of the smooth muscles induced by the administration of substance P.

To date, substance P antagonists have been administered to treat the disorders indicated above.

Nonetheless, it was hitherto unknown that a lanthanide, zinc, yttrium, tin, cobalt, barium or strontium salt exhibited a substance P antagonizing activity as defined above and thus could be useful for treating the pain associated with the various skin conditions and/or disorders indicated above.

In addition, a formulation containing cresols and strontium chloride for increasing the antibacterial and antimicrobial properties of such cresols is described in FR-M-5394. However, it is neither described nor suggested that the strontium chloride can, by itself alone, decrease or indeed eliminate symptoms such as irritation, pain, itching or smarting caused by any disease nor decrease or indeed eliminate the same symptoms elicited by an irritant product.

SUMMARY OF THE INVENTION

It has now unexpectedly and surprisingly been determined that lanthanide, manganese, tin, zinc, yttrium, cobalt, barium and strontium salts exhibit substance P antagonizing activity as defined above and therefore are useful for the treatment of and/or alleviation of pain associated with at least one of the following skin disorders, including those of the scalp and mucous membranes: zona, poszoster, scald or burns, demodicidosis, skin ulcer, fibrosis and/or controlling hypertrophic cicatrization and/or treating acne rosacea.

Thus, the present invention features the administration of at least one lanthanide, manganese, tin, zinc, yttrium, cobalt, barium or strontium salt as a substance P antagonist in a dermatological/pharmaceutical composition.

The present invention also features the administration of at least one cobalt and/or zinc salt as a substance P antagonist in a dermatological/pharmaceutical composition for the treatment and/or alleviation of pain associated with at least one of the following skin disorders, including those of the scalp and mucous membranes: zona, poszoster, scald or burns, demodicidosis, skin ulcer, fibrosis, and/or controlling hypertrophic cicatrization and/or treating acne rosacea.

DETAILED DESCRIPTION OF BEST MODE AND SPECIFIC/PREFERRED EMBODIMENTS OF THE INVENTION

More particularly according to the present invention, by "lanthanide" are intended the elements of atomic number z ranging from 57 to 71, namely, lanthanum, cerium, praseodymium, neodymium, promethium, samarium, europium, gadolinium, terbium, dysprosium, holmium, erbium, thulium, ytterbium, and lutetium.

The present invention is applicable to all of the disorders associated with an excessive synthesis and/or release of substance P that are mentioned above.

Exemplary salts according to the invention include carbonates, bicarbonates, sulfates, glycerophosphates, borates, chlorides, nitrates, acetates, hydroxides, persulfates as well as salts of α-hydroxy acids (citrates, tartrates, lactates, malates) or of the fruit acids in general, or, alternatively, salts of amino acids (aspartate, arginate, glycocholate, fumarate) or salts of fatty acids (palmitate, oleate, caseinate, behenate).

Preferably, the salts are chlorides or nitrates, advantageously of zinc, gadolinium, yttrium and strontium.

Also preferably, the salts are of zinc, barium, manganese, yttrium and strontium, and combinations thereof.

The salt is most preferably a strontium salt.

According to the present invention, the salt is advantageously formulated in an amount ranging from $10^{-5}\%$ to 20% of the total weight of the composition and, preferably, in an amount ranging from $10^{-2}\%$ to 15% of the total weight of the composition and, more preferably, from 0.5% to 8% of the total weight of the composition.

The salt can be formulated into a composition which must be ingested, injected or topically applied onto the skin (on any area of skin of the body), onto the hair and/or onto the nails. Depending on the mode of administration, this composition can be provided in any of the pharmaceutical dosage forms normally employed.

For topical application to the skin, the composition may have the form, especially, of an aqueous, aqueous-alcoholic or oily solution, or of an oily suspension, or of a dispersion of the lotion or serum type, of emulsions of liquid or semi-liquid consistency of the milk type, which are obtained by dispersing a fatty phase in an aqueous phase (O/W) or, conversely, (W/O), or of suspensions or emulsions of soft consistency of the cream type or of aqueous or anhydrous gels, of micro-emulsions or, alternatively, microcapsules or microparticles, or of vesicular dispersions of the ionic and/or nonionic type. These compositions are formulated via the usual techniques.

They may also be applied to the hair in the form of aqueous, alcoholic or aqueous-alcoholic solutions, or in the form of creams, gels, emulsions or foams.

For injection or infusion, the composition may be provided in the form of an aqueous lotion, an oily suspension, or in the form of a serum. For the eyes, it may be provided in the form of drops. Also for ingestion, it may be provided in the form of capsules, granules, syrups or tablets.

The amounts of the various constituents of the compositions according to the invention are those conventionally used in the fields under consideration.

These compositions constitute, in particular, cleansing, protecting, treatment or care creams for the face, for the hands, for the feet, for large anatomical folds or for the body (for example day creams, night creams, makeup removing creams, foundation creams, antisun or sunscreen creams), fluid foundations, makeup removing milks, body protecting or care milks, aftersun milks, lotions, gels or foams for skin care, such as cleansing lotions, aftersun lotions, artificial tanning lotions, bath compositions, deodorant compositions comprising a bactericidal agent, aftershave gels or lotions, depilatory creams, compositions against insect bites, antipain compositions, compositions for treating certain skin diseases such as eczema, rosasea, psoriasis, lichens, severe pruritus and those indicated above.

The compositions according to the invention may also comprise solid preparations, e.g., cleansing bars or soaps.

The subject compositions may also be packaged in the form of an aerosol composition, also comprising a pressurized propellant agent.

The salt according to the invention may also be incorporated into various compositions for hair care, and especially shampoos, hairsetting lotions, treatment lotions, hair-styling creams or gels, dye compositions (especially oxidation dyes) optionally in the form of coloring shampoos, restructuring lotions for the hair, permanent-waving compositions (especially compositions for the first stage of a permanent waving), lotions or gels for preventing hair loss, antiparasitic shampoos and the like.

When the composition is an emulsion, the proportion of fatty phase may range from 5% to 80% by weight, and preferably from 5% to 50% by weight relative to the total weight of the composition. The oils, waxes, emulsifiers and coemulsifiers used in the compositions in the form of an emulsion are selected from among those conventionally used in the cosmetics field. The emulsifier and the coemulsifier are present in the composition in a proportion advantageously ranging from 0.3% to 30% by weight, preferably from 0.5% to 20% by weight relative to the total weight of the composition. The emulsion may, in addition, contain lipid vesicles.

When the composition is an oily gel or solution, the fatty phase may constitute more than 90% of the total weight of the composition.

In known manner, the pharmaceutical composition may also contain adjuvants and additives normally used in the pharmaceutical field, such as hydrophilic or lipophilic gelling agents, hydrophilic or lipophilic additives, preservatives, antioxidants, solvents, perfumes, fillers, sunscreens, odor absorbers and colorants. The amounts of these various adjuvants and additives are those conventionally used in the cosmetics field, and range, for example, from 0.01% to 20% of the total weight of the composition. These adjuvants and additives, depending on their nature, may be introduced into the fatty phase, into the aqueous phase and/or into the lipid spherules.

Exemplary oils or waxes according to the invention include mineral oils, vegetable oils (soya bean oil, palm oil, liquid fraction of shea butter, sunflower oil), animal oils (perhydrosqualene), synthetic oils, silicone oils or waxes (cyclomethicone, dimethicone) and fluorinated oils (perfluoropolyethers). Fatty alcohols (cetyl alcohol), fatty acids (stearic acid) and waxes (beeswax, carnauba wax and paraffin wax) may be added to these oils.

Exemplary emulsifiers which are suitable according to the invention include glycerol stearate, PEG-100 stearate, polyglyceryl-3 hydroxylauryl ether and polysorbate 60.

Exemplary solvents which are suitable include the lower alcohols, especially ethanol and isopropanol, and propyleneglycol.

Exemplary hydrophilic gelling agents according to the invention include carboxyvinyl polymers (carbomer), acrylic copolymers such as acrylate/alkylacrylate copolymers, polyacrylamides, polysaccharides such as hydroxypropyl-cellulose, natural gums and clays. And exemplary lipophilic gelling agents include modified clays such as bentones, metallic salts of fatty acids such as aluminum stearates and hydrophobic silica, ethyl cellulose, and polyethylene.

The subject compositions may contain other hydrophilic active agents, such as proteins or protein hydrolysates, amino acids, polyols, urea, allantoin, sugars and sugar derivatives, water-soluble vitamins, vegetable or bacteria extracts and starch.

Representative lipophilic active agents include retinol (vitamin A) and derivatives thereof, tocopherol (vitamin E) and derivatives thereof, essential fatty acids, ceramides, essential oils.

According to this invention, it is envisaged to combine, inter alia, with the lanthanide, manganese, tin, zinc, yttrium, cobalt, barium and strontium salts, other active agents.

Exemplary active agents include:

(1) skin pigmentation and/or proliferation and/or differentiation modulating agents, such as retinoic acid and isomers thereof, retinol and esters thereof, vitamin D and derivatives thereof, estrogens such as estradiol, kojic acid or hydroquinone;

(2) antibacterial agents such as clindamycin phosphate, erythromycin or antibiotics of the tetracycline class;

(3) antiparasitic agents, in particular metronidazole, crotamiton or pyrethrinoids;

(4) antifungal agents, in particular the compounds belonging to the imidazole class such as econozale, ketoconazole or miconazole or salts thereof, polyene compounds such as amphotericin B, compounds of the allylamine family, such as terbinafine, or alternatively octopirox;

(5) antiviral agents such as acyclovir;

(6) steroidal anti-inflammatory agents such as hydrocortisone, betamethasone valerate or clobetasol propionate, or nonsteroidal anti-inflammatory agents such as ibuprofen and salts thereof, diclofenac and salts thereof, acetylsalicylic acid, acetaminophen or glycyrrhetinic acid;

(7) anaesthetic agents such as lidocaine hydrochloride and derivatives thereof;

(8) antipruritic agents such as thenaldine, trimeprazine or cyproheptadine;

(9) keratolytic agents such as alpha- and beta-hydroxycarboxylic or -ketocarboxylic acids, their salts, amides or esters and, more particularly, hydroxy acids such as glycolic acid, lactic acid, salicylic acid, citric acid and, in general, fruit acids, and n-octanoyl-5-salicylic acid;

(10) anti-free radical agents such as alpha-tocopherol or esters thereof, superoxide dismutases, certain metal chelators or ascorbic acid and esters thereof;

(11) antiseborrhoeic agents such as progesterone;

(12) antidandruff agents such as octopirox or zinc pyrithione;

(13) antiacne agents such as retinoic acid or benzoyl peroxide;

(14) antiseptics;

(15) antimetabolites.

Thus, in a specific embodiment of the invention, the subject compositions comprise at least one salt selected from among lanthanide, manganese, tin, zinc, yttrium, cobalt, barium and strontium salts and at least one active agent selected from among antibacterial, antiparasitic, antifungal, antiviral, anti-inflammatory, antipruritic, anaesthetic, keratolytic, anti-free radical, antiseborrhoeic, antidandruff, or anti-acne agents and/or skin pigmentation and/or proliferation and/or differentiation modulating agents.

Advantageously, at least one lanthanide, manganese, tin, zinc, yttrium, cobalt, barium or strontium salt is combined with products or species eliciting an irritant effect and which are commonly used in the dermatological/pharmaceutical field, agents which are sometimes dermatological/pharmaceutical active principles. The presence of a substance P antagonist in the form of at least one lanthanide, manganese, tin, zinc, yttrium, cobalt, barium or strontium salt in a dermatological/pharmaceutical composition comprising an active agent eliciting an irritant effect makes it possible to attenuate substantially, or even suppress or eliminate, this irritant effect. This additionally permits increasing the amount of active agent eliciting an irritant effect relative to the amount of active agent normally used, for enhanced efficacy.

The present invention also features a dermatological/pharmaceutical regimen for the treatment of at least one of the following skin disorders, including those of the scalp and mucous membranes: zona, poszoster, scald or burns, demodicidosis, skin ulcer, fibrosis and/or controlling hypertrophic cicatrization and/or treating acne rosacea.

The present invention also features a dermatological or pharmaceutical treatment regimen, especially for reducing the irritant effect of a dermatological or pharmaceutical composition, according to which a composition as described above, advantageously one comprising at least one cobalt, lanthanum, strontium and/or zinc salt, is topically applied onto the skin, onto the hair and/or onto the mucous membranes.

These treatments are advantageously carried out by applying the hygienic, dermatological or pharmaceutical compositions described above according to the usual techniques. For example: application of creams, gels, serums, lotions, makeup removing milks or aftersun or sunscreen compositions onto the skin or onto dry hair, application of a hair lotion onto wet hair, of shampoos.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Cleansing cream (Formula A)

| | | |
|---|---|---|
| Yttrium caronate | | 5.00 |
| Cetyl alcohol | | 2.00 |
| Glycerol stearate | | 2.00 |
| Stearic acid | | 2.00 |
| Polyglyceryl-3 Hydroxylauryl Ether | | 5.00 |
| Mineral oil Codex | | 12.00 |
| Carbomer | | 0.35 |
| Sodium hydroxide | | 0.15 |
| Perfume | qs | |
| Methyl Paraben | | 0.20 |
| Sterile demineralized water | qs | 100.00 |

EXAMPLE 2

Cleansing milk (Formula B)

| | | |
|---|---|---|
| Lanthanum nitrate | | 0.5 |
| Carbomer | | 0.40 |
| Sodium hydroxide | | 0.10 |
| Mineral oil Codex | | 5.00 |
| Glycerol stearate | | 1.00 |
| Cetyl alcohol | | 0.50 |
| PEG 100 stearate | | 0.80 |
| Methyl paraben | | 0.20 |
| Perfume | qs | |
| Sterile demineralized water | qs | 100.00 |

EXAMPLE 3
Care lotion (Formula C)

| | | |
|---|---|---|
| Cobalt chloride | | 0.5 |
| Glycerol | | 2.00 |
| Methyl paraben | | 0.15 |
| Perfume | qs | |
| Sterile demineralized water | qs | 100.00 |

EXAMPLE 4
Care cream (Formula D)

| | | |
|---|---|---|
| Barium chloride | | 1.00 |
| Glycerol stearate | | 1.00 |
| PEG 100 stearate | | 1.00 |
| Stearic acid | | 1.00 |
| Cetyl alcohol | | 2.00 |
| Soya bean oil | | 3.00 |
| Palm oil | | 2.00 |
| Cyclomethicone | | 2.00 |
| Dimethicone | | 1.00 |
| Polyacrylamide | | 0.20 |
| Glycerol | | 3.00 |
| Methyl paraben | | 0.20 |
| Perfume | qs | |
| Sterile demineralized water | qs | 100.00 |

EXAMPLE 5
Face care gel (Formula E)

| | | |
|---|---|---|
| Strontium chloride | | 5.00 |
| Hydroxypropylcellulose (Klucel H marketed by Hercules) | | 1.00 |
| Antioxidant | | 0.05 |
| Isopropanol | | 40.00 |
| Preservative | | 0.30 |
| Water | qs | 100% |

EXAMPLE 6
Care cream for solar crythema (oil-in-water emulsion) (Formula F)

| | | |
|---|---|---|
| Zinc aspartate | | 0.75 |
| Glycerol stearate | | 2.00 |
| Polysorbate 60 (Tween 60 marketed by ICI) | | 1.00 |
| Stearic acid | | 1.40 |
| Glycyrrhetinic acid | | 2.00 |
| Triethanolamine | | 0.70 |
| Carbomer | | 0.40 |
| Liquid fraction of the shea butter | | 12.00 |
| Sunflower oil | | 10.00 |
| Antioxidant | | 0.05 |
| Perfume | | 0.5 |
| Preservative | | 0.30 |
| Water | qs | 100% |

EXAMPLE 7
Lotion for removing scars (Formula G)

| | | |
|---|---|---|
| Glycerophosphate of strontium | | 1.5 |
| Glycolic acid | | 50.00 |
| Hydroxypropylcellulose (Klucel H) | | 0.05 |
| NaOH | qs | pH = 2.80 |

-continued

| | | |
|---|---|---|
| Ethanol | qs | 100% |
| Preservative | | 0.30 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited is solely by the scope of the following claims, including equivalents thereof.

What is claimed is:

1. A method for the therapeutic treatment or alleviation of pain associated with at least one skin disorder selected from the group consisting of zona, poszoster, scald or burns, demodicidosis, skin ulcer, fibrosis, hypertrophic cicatrization and acne rosacea, comprising administering to a mammalian subject afflicted with said at least one skin disorder, an amount of at least one substance P antagonist which is a salt comprising at least one metal selected from the group consisting of yttrium, lanthanum, cerium, praseodymium, neodymium, promethium, samarium, europium, gadolinium, terbium, dysprosium, holmium, erbium, thulium, ytterbium, lutetium, tin, manganese, barium and strontium.

2. A method for the therapeutic treatment of or alleviation of pain associated with at least one skin disorder selected from the group consisting of zona, poszoster, scald or burns, demodicidosis, skin ulcer, fibrosis, hypertrophic cicatrization and acne rosacea, comprising administering to a mammalian subject afflicted with said at least one skin disorder an amount of a substance P antagonist sufficient to prevent or alleviate pain, wherein said at least one substance P antagonist salt comprises at least one metal selected from the group consisting of zinc, barium, manganese, yttrium, and strontium.

3. The method according to claim 1 or 2, wherein said substance P antagonist salt comprises at least one anion selected from the group consisting of chloride, borate, bicarbonate, carbonate, nitrate, hydroxide, sulfate, glycerophosphate, or said salt comprises a fruit acid or an amino acid salt.

4. The method according to claim 1 or 2, wherein said at least one substance P antagonist salt comprises at least one metal selected from the group consisting of zinc, barium, manganese, yttrium, and strontium.

5. The method according to claim 4, wherein said at least one substance P antagonist salt is a strontium containing salt.

6. The method according to claim 3, wherein said at least one substance P antagonist salt is a chloride or nitrate.

7. The method according to claim 5, wherein said strontium containing salt is a chloride or nitrate.

8. The method according to claim 1 or 2, which further comprises administering to said mammalian subject at least one other active agent selected from the group consisting of an antibacterial agent, an agent for combating parasites, and antifungal agent, an antiviral agent, an anti-inflammatory agent, an antipruriginous agent, an anaesthetic agent, a keratolytic agent, an agent for combating free radicals, an antiseborrhoeic agent, an antidandruff agent, an antiacne agent, and an agent which modulates at least one of cutaneous pigmentation, proliferation and differentiation.

9. The method according to claim 1 or 2, which comprises topically applying said at least one substance P antagonist onto at least one of the skin, the hair and the mucous membranes of said mammalian subject.

10. A composition of matter suitable for dermatological or pharmaceutical usage for the therapeutic treatment or alleviation of pain associated with at least one skin disorder selected from the group consisting of zona, poszoster, scald or burns, demodicidosis, skin ulcer, fibrosis, hypertrophic cicatrization and acne rosacea, which composition of matter comprises (i) an amount of at least one substance P antagonist salt effective to treat or alleviate pain associated with said at least one skin disorder, when said at least one salt comprises at least one metal selected from the group consisting of yttrium, lanthanum, cerium, praseodymium, neodymium, promethium, samarium, europium, gadolinium, terbium, dysprosium, holmium, erbium, thulium, ytterbium, lutetium, tin, zinc, manganese, cobalt and barium;

(ii) a normally irritating amount of at least one irritant which are contained in a dermatologically or pharmaceutically acceptable medium therefore, and wherein the relative amounts are of said at least one substance P antagonists salt and said irritant are such that said salt prevents or alleviates the irritation normally associated with said irritant upon administration.

11. The dermatological or pharmaceutical composition of claim 10, wherein said at least one substance P antagonist salt comprises from $10^{-5}$ percent to 20 percent of the total weight of said composition.

12. The dermatological or pharmaceutical composition as defined by claim 11, wherein said at least one substance P antagonist salt comprises from $10^{-2}$ percent to 15 percent of the total weight of said composition.

13. The dermatological or pharmaceutical composition as defined by claim 10, wherein said irritant is an active agent.

14. The dermatological or pharmaceutical composition as defined by claim 10, which comprises an effective amount of at least one active agent selected from the the group consisting of an antibacterial agent, an agent for combating parasites, an antifungal agent, an antiviral agent, an antiinflammatory agent, an antipruriginous agent, an anaesthetic agent, a keratolytic agents, an agent for combating free radicals, an antiseborrhoeic agent, an antidandruff agent, an antiacne agent, and an agent which modulates at least one of cutaneous pigmentation, proliferation and differentiation.

15. The dermatological or pharmaceutical composition as defined by claim 10, which comprises a form selected from the group consisting of aqueous, oily or aqueous-alcoholic solution, and oil-in-water or water-in-oil emulsion, a microemulsion, an aqueous or anhydrous gel, a serum, and a dispersion of vesicles.

16. A dermatological or pharmaceutical composition of matter which is suitable for the therapeutic treatment or alleviation of pain associated with at least one skin disorder selected from the group consisting of zona, poszoster, scald or burns, demodicidosis, skin ulcer, fibrosis, hypertrophic cicatrization and acne rosacea, which composition comprises an amount of at least one substance P antagonist salt which is effective to treat or alleviate said pain associated with said at least one skin disorder, wherein said salt comprises at least one metal selected from the group consisting of yttrium, cerium, praseodymium, neodymium, promethium, samarium, europium, gadolinium, terbium, dysprosium, holmium, erbium, thulium, ytterbium, lutetium, tin, zinc, manganese, barium, and combinations thereof, wherein said substance P antagonist salt is contained in a dermatologically or pharmaceutically acceptable medium therefore.

17. The dermatological or pharmaceutical composition of claim 16, wherein said at least one salt comprises from $10^{-5}$ percent to 20 percent of the total weight of said composition.

18. The dermatological or pharmaceutical composition as defined by claim 17, wherein said at least one substance P antagonist salt comprises from $10^{-2}$ percent to 15 percent of the total weight of said composition.

19. The dermatological or pharmaceutical composition according to claim 17, wherein said composition is in a form selected from the group consisting of an aqueous, oily or aqueous-alcoholic solution, an oil-in-water, or water-in-oil emulsion, a microemulsion, an aqueous or anhydrous gel, a serum or a dispersion of vesicles.

\* \* \* \* \*